United States Patent [19]

McKinley

[11] Patent Number: 5,104,315
[45] Date of Patent: Apr. 14, 1992

[54] ORAL HYGIENE DEVICE

[76] Inventor: Earl O. McKinley, Rte. 4, Box 314, North Manchester, Ind. 46962

[21] Appl. No.: 507,457

[22] Filed: Apr. 11, 1990

[51] Int. Cl.$^5$ ............................................. A61G 5/02
[52] U.S. Cl. ..................................... 433/80; 433/216; 433/71; 128/66
[58] Field of Search ........................ 433/30, 91, 72, 68, 433/70, 71, 6, 37, 214, 216; 604/77; 128/62 A, 66

[56] References Cited

U.S. PATENT DOCUMENTS

| | | | |
|---|---|---|---|
| 803,475 | 10/1905 | Dennis | 433/80 |
| 1,500,107 | 7/1924 | Chandler | 604/77 |
| 1,840,703 | 1/1932 | Cunningham | 433/71 |
| 2,258,883 | 10/1941 | Cressler . | |
| 3,380,446 | 4/1968 | Martin . | |
| 3,527,218 | 9/1970 | Westline | 604/77 |
| 3,731,675 | 5/1973 | Kelly | 128/62 A |
| 3,840,992 | 10/1974 | English | 128/62 A |
| 4,106,501 | 8/1978 | Ozbey et al. | 433/80 |
| 4,164,940 | 8/1979 | Quinby | 433/216 |
| 4,237,574 | 12/1980 | Kelly et al. | 128/62 A |
| 4,560,351 | 12/1985 | Osborne | 433/216 |
| 4,865,021 | 12/1989 | Siderman | 128/66 |

FOREIGN PATENT DOCUMENTS 0879473 10/1961 United Kingdom .................. 604/77

*Primary Examiner*—Cary E. O'Connor
*Attorney, Agent, or Firm*—Barnes & Thornburg

[57] ABSTRACT

A mouthpiece for a dental hygiene apparatus is formed of a relatively rigid tray having a plurality of orifices connected by tubes to a source of dental cleaning solution, a vacuum source, and a vent. A first group of the orifices are selectively formed and positioned in the tray such that they lie adjacent the interproximal crevices of the teeth. These orifices are connected to the source of cleaning solution. A second group of orifices, which are substantially larger in diameter and fewer in number than the first orifices, are connected to the vacuum source for evacuating the cleaning solution and other substances from the mouth. The second orifices are formed in the tray in a position which is inferior to (i.e., below) the first orifices. A pair of third orifices are formed in the tray superior to (i.e., above) the first orifices, and are connected to a vent to prevent formation of a vacuum within the mouth during operation. The apparatus further includes a vacuum operated valve for allowing user control of the flow of cleaning solution to the mouthpiece. An additional source of cleaning solution, such as a foam presoak, may be provided through one or more of the orifices. Another aspect of the invention involves an apparatus and method for selecting one of a plurality of different size mouthpieces for use by a prospective user. The sizing apparatus includes a bite registration device and one or more templates.

39 Claims, 4 Drawing Sheets

ORAL HYGIENE DEVICE

BACKGROUND OF THE INVENTION

This invention relates generally to dental hygiene apparatus and more specifically, to mouthpieces which are used with dental hygiene apparatus. In addition, the invention relates to an apparatus and method for selecting appropriately sized mouthpieces for prospective users of the dental hygiene apparatus.

Apparatus for cleaning and polishing teeth of a type which includes a mouthpiece, a source of pressurized cleaning solution, and a vacuum pump are known in the prior art. For example, U.S. Pat. No. 3,731,675 to Kelly shows one such apparatus which includes a mouthpiece adapted to fit over a portion of the dentition of a user and to sealingly engage the gums. The Kelly mouthpiece has a plurality of interiorly disposed inlet and exhaust ports which communicate with a source of fluid or other cleansing material and an evacuation pump, respectively. The cleansing material is turbulently drawn between and around the teeth by suction from the pump to purportedly remove small food particles, bacteria and bacterial plaque, bacterial matt or organized bacteria, and to polish exposed tooth surfaces.

Other examples of prior art devices include those shown in U.S Pat. Nos. 803,475; 1,500,106; 3,379,192; 3,380,446; 3,489,141; 3,527,218; 4,106,501; 4,16,940; and 4,560,351. As in the Kelly patent, some of these devices rely upon achieving and maintaining an effective seal between the mouthpiece component and the teeth or gums of the user. This requires a relatively precise fit of the mouthpiece to the individual user, and often means that a relatively soft and pliable material must be used in forming the mouthpiece. A mouthpiece of this type may be subject to considerable wear and tear over extended periods of use and may need to be replaced more frequently than a mouthpiece which is formed of a relatively rigid, more durable material.

One problem which occurs in many dental hygiene systems which use a mouthpiece and a suction device to draw fluids from the mouth is the creation of a vacuum inside the mouth of the user. This can cause the soft tissues of the mouth to be drawn inwardly around the mouthpiece in an unintended manner. The soft tissues can obstruct inlet and outlet orifices, cause considerable discomfort to the mouthpiece user, and otherwise interfere with proper operation of the device. Providing an adequate air volume to the mouth during operation will prevent the occurrence of this problem and will increase the comfort level and overall efficiency of the cleaning apparatus.

An object of the present invention is to provide an improved mouthpiece for use with a dental hygiene apparatus.

Another object of the present invention is to provide a mouthpiece for use with a dental hygiene apparatus which is especially well-suited for use by invalid patients in hospitals, nursing homes or retirement homes.

Yet another object of the present invention is to provide a mouthpiece for use with a dental hygiene apparatus which incorporates a shut-off feature to enhance the safety and convenience of the apparatus.

Still yet another object of the present invention is to provide a method and apparatus for selecting one of a plurality of different size mouthpieces for use by a prospective user, taking such factors as jaw size, tooth size and missing teeth into consideration.

These and other objects are achieved in a mouthpiece which comprises a tray, a source of pressurized dental cleaning solution, a vacuum source, and a vent. The tray is adapted to fit within the mouth of a user, and is provided with a plurality of orifices formed in surfaces of the tray which lie adjacent the teeth. A first sub-set of orifices are connected to the source of pressurized dental cleaning solution. At least one other of the orifices is connected to the vacuum source for evacuating cleaning solution, bacteria, dislodged bacterial plaque, food particles and other debris from the mouth of the user. At least one other of the orifices is connected to the vent to prevent formation of a vacuum within the mouth during operation of the apparatus.

In one embodiment of the invention, the mouthpiece is formed from a generally U-shaped tray having an outer peripheral edge portion which lies adjacent the chewing and cutting surfaces of the teeth of the user. A wall extends generally perpendicularly from an outer perimeter of the outer peripheral edge portion of the tray such that an interior surface of the wall is disposed adjacent the vertical surfaces of the teeth when the mouthpiece is in position within the mouth of the user. A plurality of first orifices are selectively formed in and positioned along the interior surface of the wall such that the orifices lie immediately adjacent the interproximal crevices of the teeth. These orifices are connected to the source of dental cleaning solution. A plurality of second orifices are formed in a surface of the tray in a position which is inferior to (i.e., below) the first orifices. The second orifices are substantially larger in diameter and fewer in number than the first orifices, and are connected to the vacuum source for evacuating the cleaning solution from the mouth. A plurality of third orifices are formed in a surface of the tray superior to (i.e., above) the first orifices, and are connected to a separate source of fluid (such as the ambient environment) to serve as a vent and prevent formation of a vacuum within the mouth during operation of the apparatus. These third orifices are preferably located along the superior border of the interior wall of the tray.

In the embodiment described herein, the orifices open into chambers formed in the tray which, in turn, are connected by tubing to the source of dental cleaning solution, the vacuum source, and the vent, respectively. The first orifices are positioned, both vertically and laterally, along the interior surface of the wall of the tray in accordance with known relationships between tooth size and jaw size, such that each of the orifices lies adjacent an interproximal crevice in the mouth of the user. Orifices which would otherwise lie adjacent missing teeth are either not formed in the mouthpiece, or are occluded by an acrylic monomer and polymer, when appropriate. The tray is preferably formed of a relatively rigid material, such as a hard plastic. In one embodiment of the invention, separate mouthpieces are used for cleaning the upper and lower teeth. The mouthpieces are similar in construction except for the relative superior and inferior positioning of the orifices, and the interior portion of the U-shaped tray. In the mouthpiece used to clean the upper teeth, the interior portion of the tray, which is defined by an inner perimeter of the outer peripheral edge portion, is closed by a solid surface to facilitate confinement and evacuation of the cleaning solution from the mouth of the user. In the lower mouthpiece, the interior portion of the tray is open to provide clearance for the tongue of the user.

One embodiment of the mouthpiece of the present invention comprises means on the mouthpiece for controlling a flow of the cleaning solution when the mouthpiece is operably positioned in the mouth of the user. The means for controlling the flow of cleaning solution is preferably operable by the tongue of the user, and preferably comprises an orifice, a vacuum controlled valve, and means for connecting the orifice to the vacuum controlled valve such that blocking and unblocking the orifice with the tongue causes the valve to open and close to control the flow of cleaning solution to the mouthpiece. The orifice is positioned on the mouthpiece so as to be blocked when the tongue is in a forward position and unblocked when the tongue is withdrawn toward the throat, as would occur in response to the normal gag reflex of the user.

One embodiment of the invention further comprises means for alternatively connecting the second orifices to a second source of dental cleaning solution, such as a foam presoak solution. In this embodiment, the presoak solution is supplied to the mouth of the user through the second orifices for a predetermined presoaking period. Following the presoak, the solution is evacuated through the second orifices prior to, or concurrently with, the beginning of the cleaning operation.

Another aspect of the present invention involves an apparatus and method for selecting one of a plurality of different size mouthpieces for use by a prospective user. The apparatus comprises bite registration means for measuring and recording the bite pattern formed by the teeth of the prospective user, and template means for comparing the recorded bite pattern to each of a plurality of different size mouthpieces and determining which of the plurality of mouthpieces is closest in size to the recorded bite pattern. The bite registration means preferably comprises a Y-shaped wafer having an upper layer, a lower layer, and a separating membrane. Each of the upper and lower layers is formed of a wax having an identifiable color. Impressions formed in the wax provide a record of the bite pattern of the user. The template preferably comprises one or more transparent plate having a plurality of markings thereon, which are indicative of the relative sizes of the plurality of mouthpieces. After the bite pattern is measured and recorded in the Y-shaped wafer, the wafer is compared to the markings on the template to determine which mouthpiece is most suitable for the prospective user.

Other objects, advantages and novel features of the present invention will become apparent from the following detailed description of the invention when considered in conjunction with the accompanying drawings.

DETAILED DESCRIPTION OF THE DRAWINGS

Figure 1:
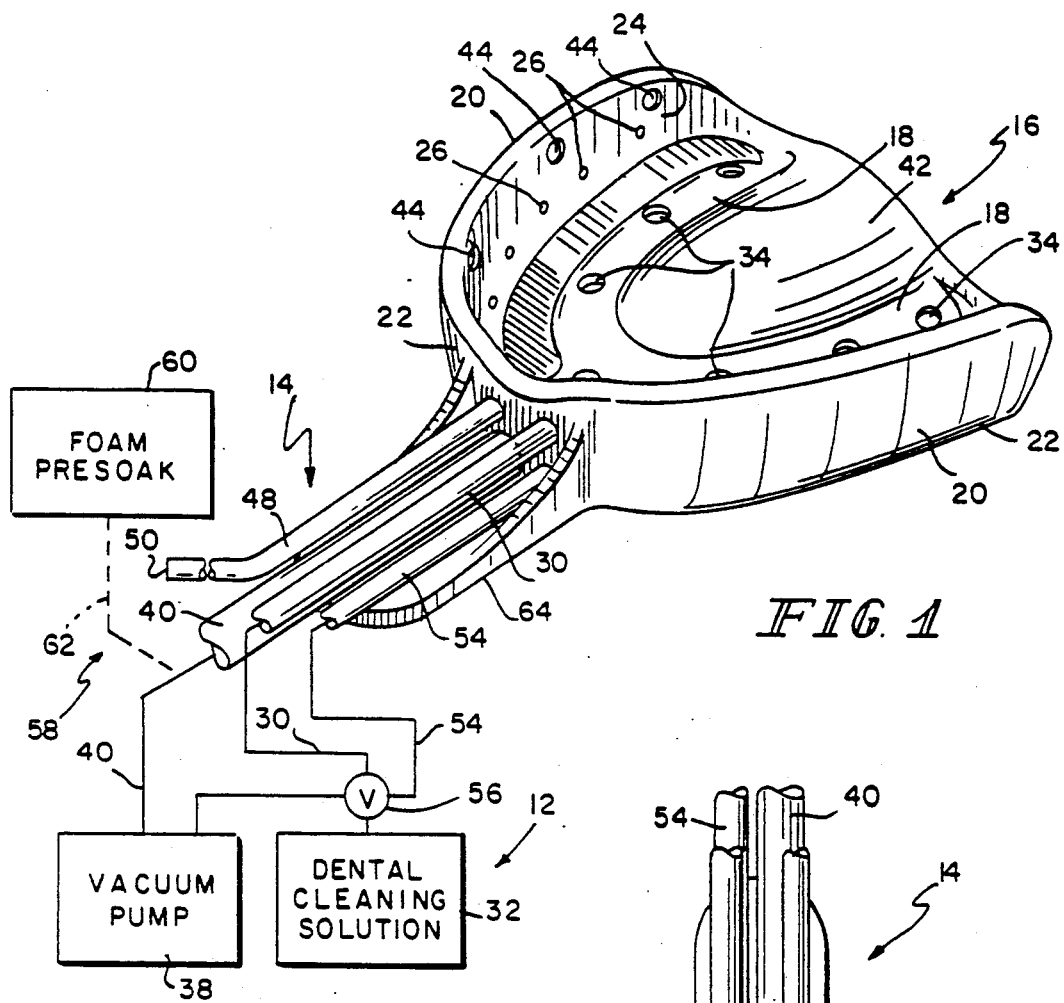
FIG. 1 is a diagrammatic view of a preferred embodiment of the mouthpiece of the present invention and the associated dental hygiene apparatus.

FIG. 1 shows a perspective view of a mouthpiece 10 which is connected to a diagrammatically illustrated dental hygiene apparatus 12 by a plurality of tubes 14. Mouthpiece 10 comprises a tray 16 which is preferably formed of a relatively rigid material, such as a hard plastic. Tray 16 is adapted to fit within the mouth of a user, and is somewhat similar to an impression tray of the type commonly used to make a mold for fabricating dentures and other orthodontic appliances. Tray 16 is generally U-shaped, and has an outer peripheral edge portion 18 which is disposed adjacent the chewing and cutting surfaces of the teeth when the mouthpiece is operatively positioned in the mouth of a user. Tray 16 additionally has a wall 20 extending generally perpendicularly from an outer perimeter 22 of outer peripheral edge portion 18 such that an interior surface 24 of wall 20 is disposed adjacent the vertical surfaces of the teeth when the mouthpiece is operatively positioned within the mouth of the user. Mouthpiece 16 is further provided with a plurality of orifices whose locations and functions will be discussed in connection with FIGS. 2, 3 and 4. A first subset of orifices 26 are formed in interior surface 24 of wall 20. Orifices 26 are positioned, both vertically and laterally along interior surface 24, in accordance with known relationships between tooth size and jaw size, such that each of orifices 26 lies Simply restated, the positioning of orifices 26 is determined in accordance with the size of the teeth of the user, which correlates with the size of the user's jaw, so that each orifice will be situated immediately adjacent an interproximal crevice formed by laterally abutting teeth. In the event that the user has one or more teeth missing, the appropriate orifice or orifices 26 may be occluded by application of an acrylic monomer and polymer.

Orifices 26 open into a chamber 28 (FIG. 3) formed in wall 20. Chamber 28, in turn, is connected by tube 30 to a source of dental cleaning solution 32. The dental cleaning solution used may be a specially formulated compound designed to remove and/or inhibit stains, deposits of plaque or calculus, bacteria, food, and other substances. Alternatively, pure water or a mixture of water and commonly used dental cleaning additives may be used. The dental cleaning solution is preferably supplied to mouthpiece 10 by unit 32 under a positive pressure which may be constant or pulsating. The pressure of the incoming fluid is preferably adjustable over a designated range.

Figure 2:
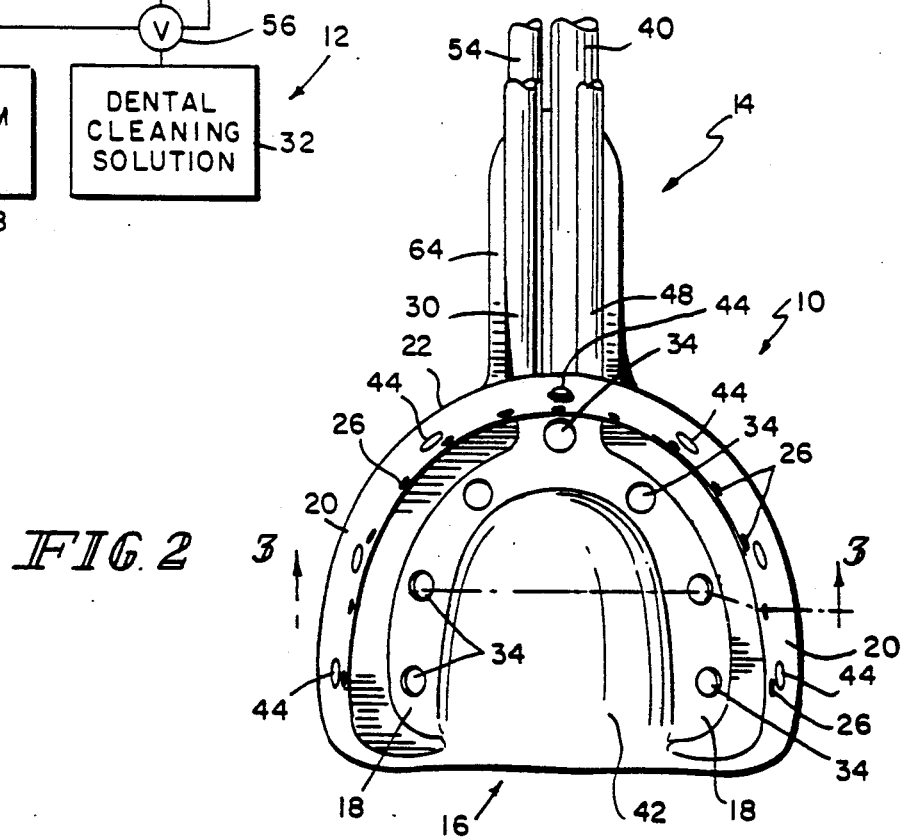
FIG. 2 is a top view of an embodiment of the mouthpiece of the present invention which is especially well-suited for cleaning the upper teeth of a user.
Figure 3:
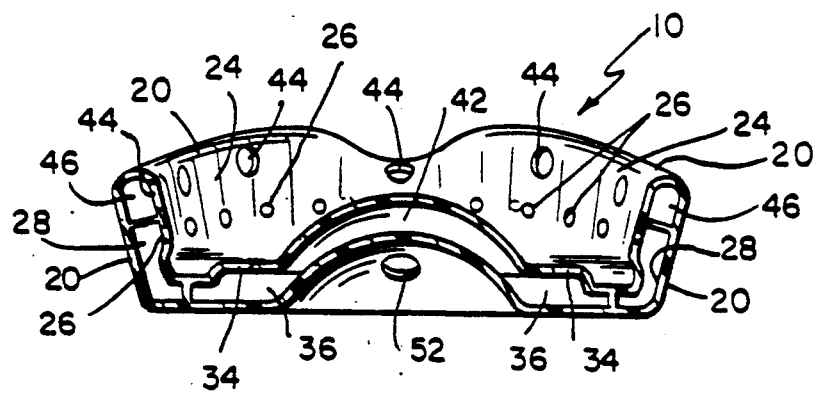
FIG. 3 is a cross-sectional view of the mouthpiece shown in FIG. 2, taken along line 3—3 of FIG. 2.

Mouthpiece 10 is further provided with a second set of orifices 34 which, in the embodiment shown in FIGS. 1-3, are located in a surface of the peripheral edge portion 18 of tray 16. Orifices 34 open into a chamber 36 (FIG. 3) which, in turn, is connected to a vacuum pump 38 by tube 40. Orifices 34 are substantially larger in diameter and fewer in number than orifices 26, and are disposed inferiorly to (i.e., below) orifices 26. Cleaning solution is provided, under pressure, through orifices 26 and directed against the interproximal crevices of the teeth of the user. The cleaning solution then flows over the flat surfaces of the teeth and downwardly into tray 16 for evacuation through orifices 34.

The used cleaning solution, as well as plaque, food particles and other debris, is confined for evacuation through orifices 34 by the closed construction of tray 16. Outer peripheral edge portion 18 is U-shaped, and has an inner perimeter which defines a solid U-shaped portion 42. As is best illustrated in FIG. 3, portion 42 is arched upwardly to conform to the inner surface or roof of the mouth of the user.

In addition to orifices 26 and 34, mouthpiece 10 has a third set of orifices 44 which, in the embodiment illustrated in FIGS. 1-3 are disposed around the superior border of wall 20 in generally opposing relation to orifices 34. Orifices 44 open into chamber 46 (FIG. 3) which, in turn, communicates with tube 48. Orifices 44 serve as vents to admit fluid, such as air, to the mouth during operation of the cleaning apparatus to prevent formation of a vacuum within the mouth during operation of the apparatus. Formation of a vacuum in the mouth during operation may cause the soft tissues surrounding the mouthpiece to be attracted to the mouthpiece, resulting in user discomfort and sub-optimal operation of the apparatus. In the embodiment illustrated in FIG. 1, tube 48 opens directly into the atmosphere at 50. Alternatively, tube 48 can be connected to a pressurized or non-pressurized bottled or otherwise confined fluid source.

Orifices 44 are disposed superiorly to (i.e., above) orifices 26 and 34. This prevents unwanted fluid entry into orifices 44, and promotes their proper functioning as a vent to the build-up of negative pressure within the mouth. Although venting is achieved in the embodiment illustrated by orifices formed in a surface of tray 16 and a chamber formed within the tray, alternative constructions are possible. For example, venting can also be achieved by a tube which opens directly into the mouth and which extends posteriorly along the mouthpiece to a point where the venting function can be achieved. Openings in the tube would perform the venting function comparably to orifices 44.

An additional feature of mouthpiece 16 illustrated in FIGS. 1-4 involves the provision of means for controlling the flow of cleaning solution to the mouthpiece when the mouthpiece is operably positioned within the mouth of a user. This means for controlling the flow of cleaning solution is preferably operable by the user of the mouthpiece, and, in the illustrated embodiment, is operable by the tongue of the user. With reference to FIG. 3, such means comprises orifice 52 which is formed in the underside of portion 42 of tray 16 toward the anterior or front end of tray 16. Orifice 52 is connected to tube 54 which, in turn, is connected to a vacuum operated valve 56 which is connected between the source of dental cleaning solution 32 and tube 30. When the tongue of the user is placed over orifice 52, valve 56 allows dental cleaning solution to flow through tube 30 to mouthpiece 10. When the tongue is removed from orifice 52, the flow of cleaning solution is interrupted by valve 56. Orifice 52 is positioned anteriorly in tray 16 so as to be blocked when the tongue is in a forward position and unblocked when the tongue is withdrawn toward the throat as would occur in response to the normal gag reflex of the user.

An additional feature which may be incorporated into the apparatus illustrated in FIG. 1 is shown in dashed lines at 58. This feature provides for a second source 60 of dental cleaning solution, such as a foam presoak, which may be alternatively connected by tube 62 to tube 40. A connection arrangement (not illustrated) will allow the foam presoak to be supplied through orifices 34 to the cutting and chewing surfaces of the teeth during or prior to the other parts of the cleaning cycle. The foam presoak is evacuated from the mouth in the same manner as the cleaning solution from unit 32. Alternatively, a separate tube and separate orifices connecting source 60 with the interior of the mouth can be provided.

In the embodiments illustrated, tubes 30, 40, 48 and 54 are joined to the mouthpiece at the approximate center of the anterior portion of wall 20. A handle 64 is formed on the mouthpiece at the same location. Handle 64 provides a convenient means for grasping and manipulating mouthpiece 10, and provides reinforcement for the above-referenced tubing at their respective points of connection to tray 16.

Figure 4:
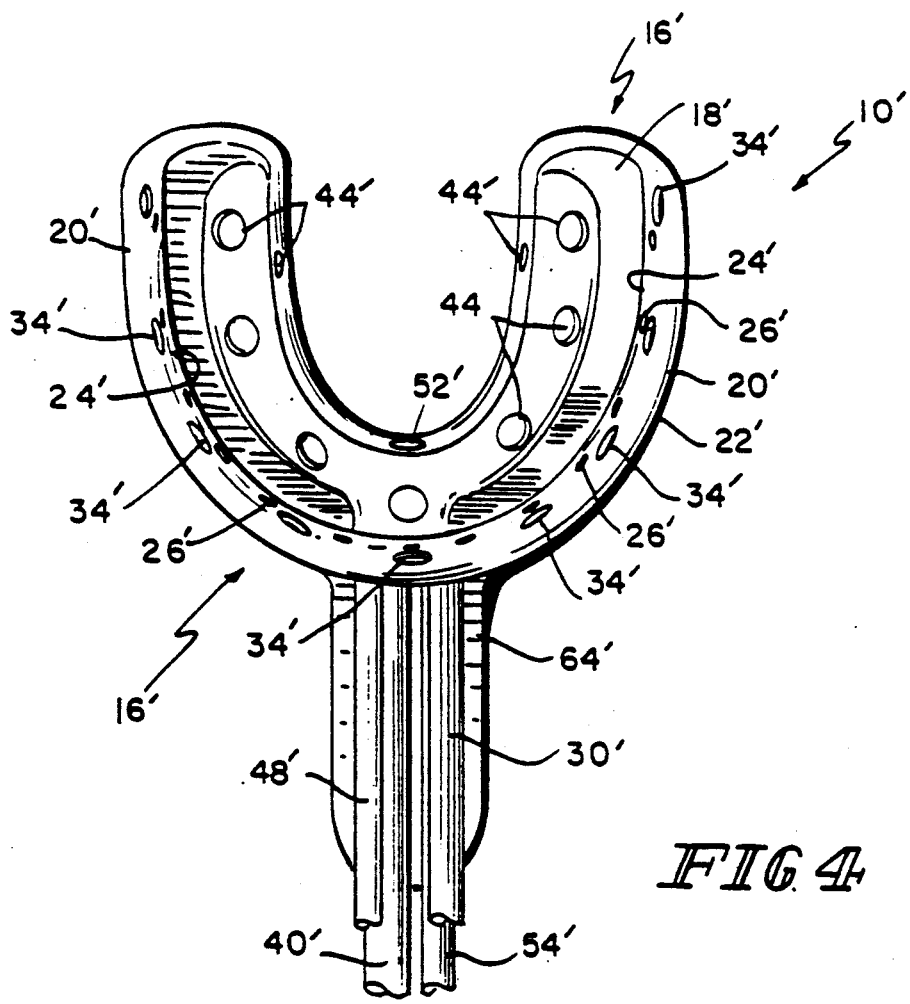
FIG. 4 is a top view of an embodiment of the mouthpiece of the present invention which is especially well-suited for cleaning the lower teeth of a user.

FIG. 4 shows an embodiment of the mouthpiece of the present invention which is especially well-suited for use in cleaning the lower teeth of the user. The mouthpiece of FIG. 4 is similar in many respects to mouthpiece 10 of FIGS. 1-3. Accordingly, like reference numerals with the addition of a "prime" will be used for designating like features where appropriate. FIG. 4 shows a mouthpiece 10' which comprises a U-shaped tray 16' which is formed of a rigid material, such as a hard plastic. Tray 16' has a generally flat edge portion 18' which is horizontally disposed when mouthpiece 10' is operably positioned in the mouth of the user. A vertical wall 20' extends downwardly (when the mouthpiece is operably positioned in the mouth) from portion 18' around the outer perimeter 22' such that an interior vertical surface 24' is disposed immediately adjacent the vvertical surfaces of the lower teeth. A plurality of orifices 26' are formed in vertical wall 24' and, as with orifices 26 of mouthpiece 10, are vertically and laterally located so as to lie adjacent the interproximal crevices of the lower teeth of the user. Orifices 26' open into a chamber (not shown) which, in turn, is connected by tube 30' to a source of a pressurized source of dental cleaning solution.

Mouthpiece 10' is provided with a second set of orifices 34' which also open into a chamber (not shown) which is connected by tube 40' to a vacuum pump. However, mouthpiece 10' differs from mouthpiece 10 in that orifices 34' are disposed along the inferior border of wall 20', so as to maintain an inferior relationship, relative to orifices 26', when the mouthpiece is positioned within the mouth of the user. In other words, orifices 34' are positioned in a surface of wall 20' so as to be maintained at a position below orifices 26' to assure adequate evacuation of cleaning solution during operation.

Another distinction between mouthpiece 10' and 10 relates to the portion of tray 16' which borders the inner perimeter of peripheral edge portion 18'. As illustrated in FIG. 4, mouthpiece 10' is of "open" construction, and is not provided with a portion which corresponds to solid U-shaped portion 42 of mouthpiece 10. This open construction provides adequate clearance for the tongue of the user.

Mouthpiece 10' is also provided with a third set of orifices 44' which serve as a vent to prevent the build-up of negative pressures within the mouth during operation. Orifices 44' are formed in a surface of outer peripheral portion 18' of tray 16', and are disposed superiorly to orifices 26'. Orifices 44' open into a chamber 46' (not shown) which is connected by tube 48' to a source of venting fluid, such as the ambient air. Orifices 44' may also be used to provide a cleaning solution, such as a foam presoak, to the cutting and chewing surfaces of the teeth. Finally, mouthpiece 10' is provided with an additional orifice 52 which is connected by tube 54 to a vacuum operated control valve (such as valve 56) to allow for user control of the supply of pressurized cleaning solution provided through orifices 26'.

Figure 5:
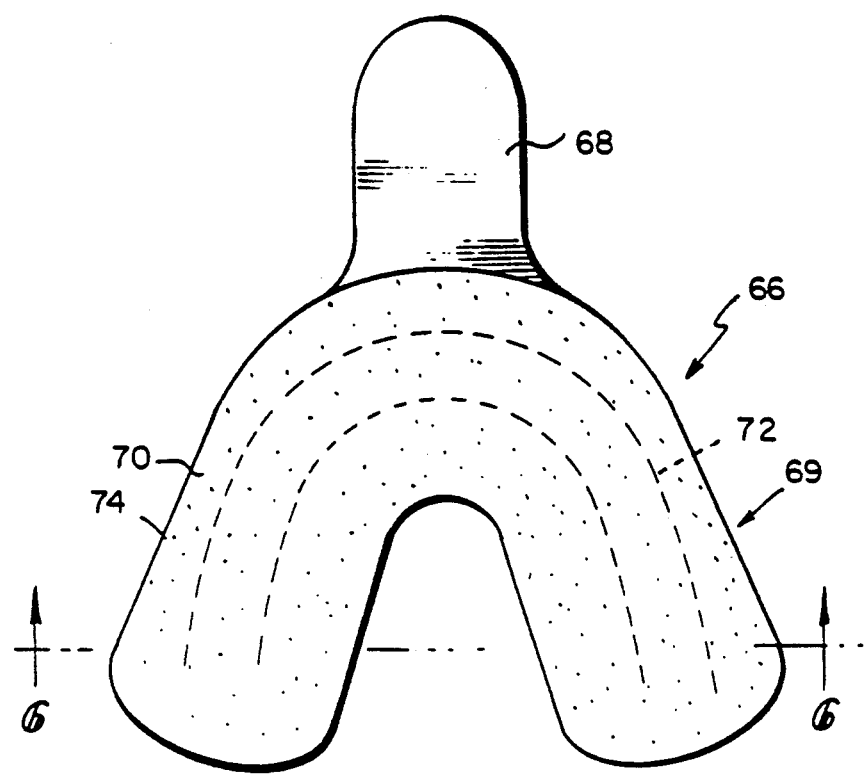
FIG. 5 shows a plan view of a bite registration wafer used in connection with the present invention.
Figure 6:
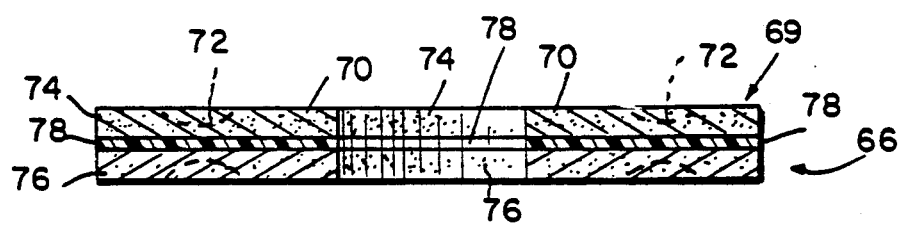
FIG. 6 is a cross-sectional view of the bite registration wafer of FIG. 5, taken along line 6—6 of FIG. 5.

FIGS. 5, 6, 7a and 7b show apparatus useful in sizing mouthpieces of the types shown and discussed above for use by prospective users. FIG. 5 shows a bite registration device 66 which is used for measuring and recording the bite pattern formed by the teeth of the prospective user. Y-shaped wafer 66 is a wishbone-shaped device having a handle portion 68 and a portion 69 which is inserted in the mouth between the teeth of the user. The user bites down on portion 70 in the area generally indicated by dashed line 72. With reference to the cross-section of portion 70 shown in FIG. 6, it can be seen that wafer 66 has an upper layer 74, a lower layer 76, and a separating membrane 78 disposed between the upper and lower layers. Upper layer 74 and lower layer 76 are formed of a wax-like substance. Layer 74 is formed of wax of a first color and lower layer 76 is formed of wax of a second color. Membrane 78 is a pliable, sheet-like material suitable for cushioning the bite while preventing penetration of the upper and lower layers, respectively, by the teeth. In measuring and recording a bite pattern, portion 70 of wafer 66 is inserted in the mouth and the teeth are closed to form impressions in upper and lower layers 74 and 76. These impressions are recorded in the wax-like substance. The color differences between top layer 74 and lower layer 76 allow the respective bite patterns of the upper and lower teeth to be distinguished.

Figure 7A:
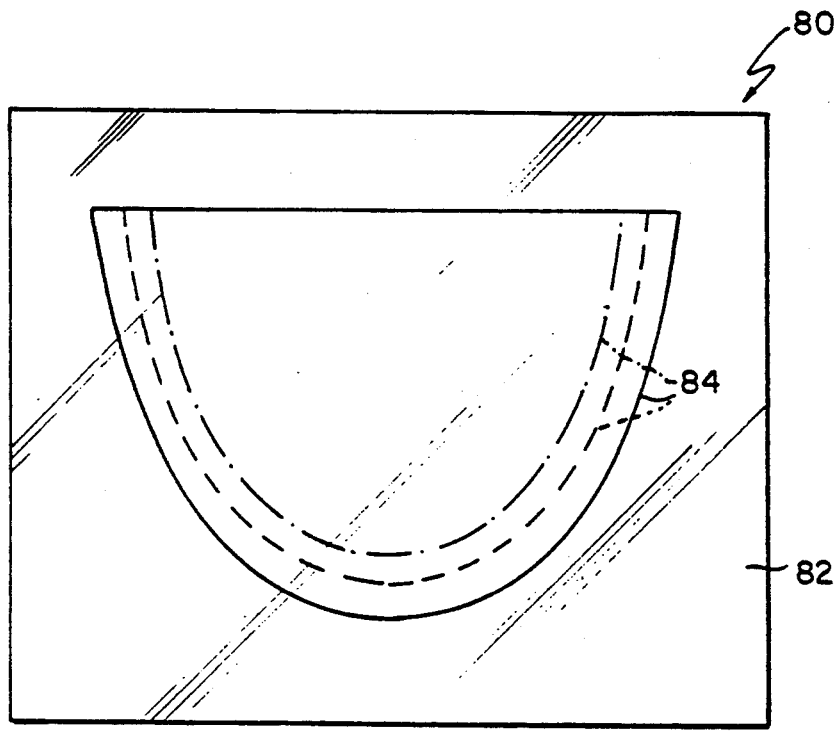
FIGS. 7a and 7b are plan views of templates which are used in choosing mouthpieces of an appropriate size for a prospective user.
Figure 7B:
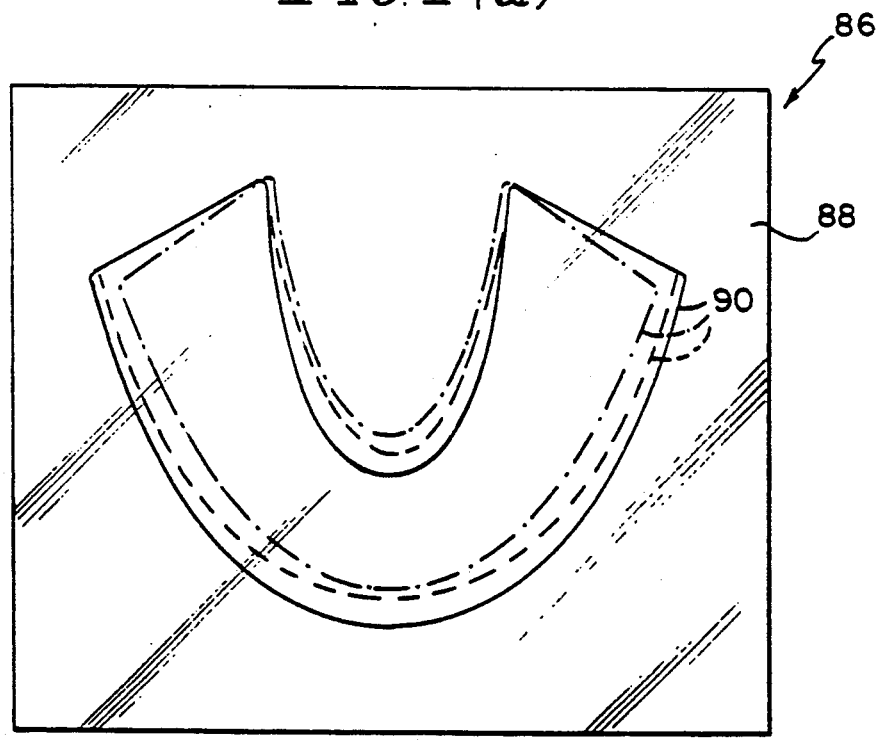

FIGS. 7a and 7b show templates 80 and 86, respectively, which are used for comparing the recorded bite patterns to each of a plurality of different size mouthpieces, and for determining which of the plurality of different size mouthpieces are closest in size to the recorded bite patterns. Template 80 comprises a transparent plate 82 having a plurality of markings 84 thereon. Markings 84 are indicative of the relative sizes of a plurality of mouthpieces of the type shown in FIGS. 1-3 which are used for cleaning the upper teeth. Template 86 comprises a transparent plate 88 having a plurality of markings 90 thereon. Markings 90 are indicative of the relative sizes of a plurality of mouthpieces of the type shown in FIG. 4 which are used for cleaning the lower teeth.

When selecting upper and lower mouthpieces of the types shown in FIGS. 1-4 above for a particular user, bite registration is measured and recorded using a wafer of the type shown in FIG. 5. Wafer 66 bearing the recorded bite pattern is then placed on template 80 and compared to the lines 84 to determine the appropriate size upper mouthpiece for the prospective user. Wafer 66 is then placed on template 86 to determine the appropriate size lower mouthpiece for the prospective user. Applicant believes that five different size upper and lower mouthpieces will be sufficient to provide an adequate fit for most users of the apparatus. However, more or fewer sizes can be represented by placing more or fewer markings 84 on templates 80 and 86. Alternatively, separate templates for separate size mouthpieces may also be used.

From the preceding description of the preferred embodiments, it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. A mouthpiece for use with a dental hygiene apparatus, comprising:
   a tray adapted to fit within the mouth of a user such that the chewing and cutting surfaces of the teeth of the user are disposed adjacent an outer peripheral edge portion of the tray;
   a wall expanding generally perpendicular from an outer perimeter of the outer peripheral edge portion of the tray such that an interior such of the wall is disposed adjacent the vertical surfaces of the teeth of the user when the mouthpiece is in position within the mouth of the user;
   a plurality of first orifices selectively formed in and positioned along the interior surface of the wall such that the orifices lie immediately adjacent the interproximal crevices of the teeth of the user;
   means for connecting the first orifices too a source of dental cleaning solution;
   a plurality of second orifices formed in a surface of the tray and disposed inferiorly relative to the first orifices, said second orifices being substantially larger in diameter and fewer in number than said first orifices;
   means for connecting the second orifices to a vacuum source for evacuating the cleaning solution from the mouth,
   at least one third orifice formed in a surface of the tray and disposed superiorly relative to the first orifices, and
   means for connecting the third orifice to a fluid source to prevent formation of a vacuum within the mouth during operation of the apparatus.

2. A mouthpiece according to claim 1, wherein said third orifice communicates with ambient air outside the mouth of the user to prevent the build-up of negative pressure within the mouth and the attraction of soft tissues to the mouthpiece during operation of the apparatus.

3. A mouthpiece according to claim 1, wherein said third orifice is formed in a surface of the wall, superiorly to said first orifices, and said second orifices are formed in a surface of the outer peripheral edge portion of the tray adjacent the cutting and chewing surfaces of the teeth, inferiorly to said first orifices.

4. A mouthpiece according to claim 1, wherein said third orifice is formed in a surface of the outer peripheral edge portion of the tray, superiorly to said first orifices, and said second orifices are formed in a surface of the wall, inferiorly to said first orifices.

5. A mouthpiece according to claim 1, wherein said means for connecting the third orifice to the fluid source comprises a chamber formed in the mouthpiece immediately adjacent said third orifice, said orifice opening into said chamber, and means for connecting the chamber to the fluid source.

6. A mouthpiece according to claim 1, wherein said means for connecting the first orifices to the source of cleaning solution comprises a chamber, formed in the wall of the mouthpiece immediately adjacent said first orifices, said orifices opening into said chamber, and means for connecting the first chamber to the source of dental cleaning solution.

7. A mouthpiece according to claim 1, wherein said means for connecting the second orifices to the vacuum source comprises a chamber, formed in the mouthpiece immediately adjacent said second orifices, said orifices opening into said chamber, and means for connecting the chamber to the vacuum source.

8. A mouthpiece according to claim 1, wherein said first orifices are positioned, vertically and laterally, along the interior surface of the wall in accordance with predetermined relationships between tooth size and jaw size, such that each of said first orifices lies adjacent an interproximal crevice in the mouth of the user.

9. A mouthpiece according to claim 1, wherein said outer peripheral edge portion defines a U-shaped tray, and wherein an interior portion of the U-shaped tray, defined by ann inner perimeter of the outer peripheral edge portion, is open to provide clearance for the tongue of the user.

10. A mouthpiece according to claim 1, wherein said outer peripheral edge portion defines a U-shaped tray, and wherein an interior portion of the U-shaped tray, defined by an inner perimeter of the outer peripheral edge portion, is closed by a solid surface to facilitate confinement and evacuation of the cleaning solution from the mouth of the user.

11. A mouthpiece for use with a dental hygiene apparatus, comprising:
   a tray adapted to fit within the mouth of a user such that the chewing and cutting surfaces of the teeth of the user are disposed adjacent an outer peripheral edge portion of the tray;
   a wall extending generally perpendicularly from an outer perimeter of the outer peripheral edge portion of the tray such that an interior surface of the wall is disposed adjacent the vertical surfaces of the teeth of the user when the mouthpiece is in position within the mouth of the user;
   a plurality of first orifices selectively formed in and positioned along the interior surface of the wall such that the orifices lie immediately adjacent the interproximal crevices of the teeth of the user;
   means for connecting the first orifices to a source of dental cleaning solution;
   a plurality of second orifices formed in a surface of the tray and disposed inferiorly relative to the first orifices, said second orifices being substantially larger in diameter and fewer in number than said first orifices;
   means for connecting the second orifices to a vacuum source for evacuating the cleaning solution from the mouth; and
   means on the mouthpiece for controlling a flow of the cleaning solution when the mouthpiece is operably positioned within the mouth of the user, said means for controlling the flow of cleaning solution being operable by the tongue of the user of the mouthpiece.

12. A mouthpiece for use with a dental hygiene apparatus, comprising:
   a tray adapted to fit within the mouth of a user such that the chewing and cutting surfaces of the teeth of the user are disposed adjacent an outer peripheral edge portion of the tray;
   a wall extending generally perpendicularly from an outer perimeter of the outer peripheral edge portion of the tray such that an interior surface of the wall is disposed adjacent the vertical surfaces of the teeth of the user when the mouthpiece is in position within the mouth of the user;
   a plurality of first orifices selectively formed in and positioned along the interior surface of the wall such that the orifices lie immediately adjacent the interproximal crevices of the teeth of the user;
   means for connecting the first orifices to a source of dental cleaning solution;
   a plurality of second orifices formed in a surface of the tray and disposed inferiorly relative to the first orifices, said second orifices being substantially larger in diameter and fewer in number than said first orifices;
   means for connecting the second orifices to a vacuum source for evacuating the cleaning solution from the mouth; and
   means on the mouthpiece for controlling a flow of the cleaning solution when the mouthpiece is operably positioned within the mouth of the user, said means for controlling the flow of cleaning solution comprising at least one of said plurality of orifices, a vacuum-controlled valve means, and means for connecting the orifice too the vacuum-controlled valve means such that blocking and unblocking the orifice with the tongue causes said valve means to open and close to control the flow of cleaning solution to the mouthpiece.

13. A mouthpiece according to claim 12, wherein said orifice is positioned so as to be blocked when the tongue is in a forward position and unblocked when the tongue is withdrawn toward the throat as would occur in response to the gag reflex of the user.

14. A mouthpiece for use with a dental hygiene apparatus, comprising:
   a tray adapted to fit within the mouth of a user, said tray having a plurality of orifices formed therein;
   means for connecting a sub-set of said orifices to a source of a pressurized dental cleaning solution;
   means for connecting at least one of said orifices to a vacuum source for evacuating the cleaning solution from the mouth of the user; and
   means for connecting at least one of said orifices to a fluid source to prevent formation of a vacuum within the mouth during operation of the apparatus.

15. A mouthpiece according to claim 14, wherein the orifice connected to the vacuum source is substantially larger in diameter than each of the sub-set of orifices connected to the source of cleaning solution.

16. A mouthpiece according to claim 14 wherein said tray is a generally U-shaped tray having an outer peripheral edge portion and a wall extending generally perpendicularly from an outer perimeter of the outer peripheral edge portion, and wherein a surface of the wall is disposed adjacent the vertical surfaces of the teeth when the mouthpiece is positioned within the mouth of the user.

17. A mouthpiece according to claim 16 wherein said sub-set of orifices are selectively formed in and positioned along the surface of the wall such that the orifices lie immediately adjacent the interproximal crevices of the teeth of the user.

18. A mouthpiece according to claim 17, wherein said orifices are positioned, vertically and laterally, along the surface of the wall in accordance with predetermined relationships between tooth size and jaw size, such that each of said first orifices lies adjacent an interproximal crevice in the mouth of the user.

19. A mouthpiece according to claim 14, wherein said mouthpiece is formed of a relatively rigid material.

20. A mouthpiece according to claim 14, wherein said means for connecting the sub-set or orifices to the source of cleaning solution comprises a chamber, formed in the tray immediately adjacent each of the sub-set of orifices, said orifices opening into said chamber, and means for connecting the chamber to the source of dental cleaning solution.

21. A mouthpiece according to claim 14, wherein said means for connecting the orifice to the vacuum source comprises a chamber, formed in the tray immediately adjacent said orifice, said orifice opening into said chamber, and means for connecting the chamber to the vacuum source.

22. A mouthpiece according to claim 14, wherein said means for connecting the orifice to the fluid source comprises a chamber, formed in the tray immediately adjacent said orifice, said orifice opening into said chamber, and means for connecting the chamber to the fluid source.

23. A mouthpiece according to claim 14, further comprising means mounted on the mouthpiece for controlling a flow of the cleaning solution when the mouthpiece is operably positioned within the mouth of the user.

24. A mouthpiece according to claim 14, further comprising means for connecting at least one of said orifices to a second source of dental cleaning solution.

25. A mouthpiece according to claim 24, wherein the second source of dental cleaning solution is a foam pre-soak solution.

26. A mouthpiece for use with a dental hygiene apparatus, comprising:
a tray adapted to fit within the mouth of a user, said tray having a plurality of orifices formed therein;
means for connecting a sub-set of said orifices to a source of pressurized dental cleaning solution;
means for connecting at least one of said orifices to a vacuum source for evacuating the cleaning solution from the mouth of the user; and
means for connecting at least one of said orifices to a vent to prevent formation of a vacuum within the mouth during operation of the apparatus, said orifice connected to the vacuum source being located inferiorly, relative to the sub-set of orifices connected to the source of cleaning solution, and said orifice connected to the vent being located superiorly, relative to said sub-set of orifices.

27. A mouthpiece for use with a dental hygiene apparatus, comprising:
a tray adapted to fit within the mouth of a user, said tray having a plurality of orifices formed therein;
means for connecting a sub-set of said orifices to a source of pressurized dental cleaning solution;
means for connecting at least one of said orifices to a vacuum source for evacuating the cleaning solution from the mouth of the user;
means for connecting at least one of said orifices to a vent to prevent formation of a vacuum within the mouth during operation of the apparatus; and
means mounted on the mouthpiece for controlling a flow of the cleaning solution when the mouthpiece is operably positioned within the mouth of the user, said means for controlling the flow of the user, said means for controlling the flow of cleaning solution being operable by the tongue of the user of the mouthpiece.

28. A mouthpiece for use with a dental hygiene apparatus, comprising:
a tray adapted to fit within the mouth of a user, said tray having a plurality of orifices formed therein;
means for connecting a sub-set of said orifices to a source of pressurized dental cleaning solution;
means for connecting at least one of said orifices to a vacuum source for evacuating the cleaning solution from the mouth of the user;
means for connecting at least one of said orifices to vent to prevent formation of a vacuum within the mouth during operation of the apparatus; and
means mounted on the mouthpiece for controlling a flow of the cleaning solution when the mouthpiece is operably positioned within the mouth of the user, said means for controlling the flow of cleaning solution comprising at least one of said plurality of orifices, a vacuum-controlled valve means, and means for connecting the orifice to the vacuum-controlled valve means such that blocking and unblocking the orifice with the tongue causes said valve means to open and close to control the flow of cleaning solution to the mouthpiece.

29. A mouthpiece according to claim 28, wherein said orifice is positioned so as to be blocked when the tongue is in a forward position and unlocked when the tongue is withdrawn toward the throat as would occur in response to the gag reflex of the user.

30. Apparatus for selecting one of a plurality of different size mouthpieces for use by a prospective user, comprising:
bite registration means for measuring and recording the bite pattern formed by the teeth of the prospective user; and
template means for comparing the recorded bite pattern to each of said plurality of different size mouthpieces and for determining which of the plurality of different size mouthpieces is closest in size to the recorded bite pattern, said bite registration mans comprising a Y-shaped wafer having an upper layer, a lower layer and a separating membrane disposed between the upper and lower layers, said upper layer comprising a wax of a first color and said lower layer comprising a wax of a second color and said membrane comprising a pliable, sheet-like material.

31. A method for selecting one of a plurality of different size mouthpieces for use by a prospective user, comprising the steps of:
(a) measuring and recording the bite pattern formed by the teeth of the prospective user; and
(b) comparing the recorded bite pattern to each of the plurality of different size mouthpieces and determining which mouthpiece is closest in size to the bite pattern of the prospective user.

32. The method according to claim 31, wherein said step of comparing the recorded bite pattern to each of said plurality or different size mouthpieces includes comparing the bite pattern to a template which comprises a transparent plate having a plurality of markings thereon, said markings being indicative of the relative sizes of the plurality of different size mouthpieces.

33. A mouthpiece identification system comprising:
a plurality of different size mouthpieces, each mouthpiece being configured and sized to fit into the mouth of a predetermined class of prospective users, each mouthpiece including a surface defining a mouthpiece pattern indicative of the configuration and size of said each mouthpiece, bite registration means for measuring and recording the bite pattern formed by the teeth of a prospective user of a mouthpiece, and template means for comparing the recorded bite pattern to the mouthpiece pattern defined by each of the plurality of different size mouthpieces so that the mouthpiece defining a mouthpiece pattern closest in size t the recorded bite pattern can be identified by a user of the template means.

34. System according to claim 33, wherein said template means comprises a transparent plate having a plurality of markings thereon, said markings being indicative of the relative sizes of the plurality of mouthpieces.

35. System according to claim 33, wherein the bite registration means includes a wafer including means for taking a first impression of teeth in an upper jaw of the prospective user of a mouthpiece and a second impression of teeth in a lower jaw of the prospective user inn response to a bite on the wafer by the prospective user of the mouthpiece while the wafer is extant in the mouth of the prospective user.

36. System according too claim 35, wherein the taking means includes a wax of a first color positioned to engage the teeth in said upper jaw and a wax of a second color position to engage the teeth in said lower jaw.

37. System according to claim 33, wherein the plurality of different size mouthpieces includes a first collection of different size upper jaw mouthpieces and a second collection of different size lower jaw mouthpieces.

38. A mouthpiece for use with a dental hygiene apparatus, comprising:

a tray configured to fit within the mouth of a user, the tray being formed to include a plurality of orifices, means for applying a dental cleaning solution to the teeth of the user through the orifices formed in the tray while the tray is situated in the mouth of the user, and means for connecting at least one of the orifices to a fluid source too prevent formation of a vacuum within the mouth during application of the dental cleaning solution to the teeth of the user.

39. A mouthpiece according to claim 38, wherein the connecting means includes a chamber formed in the tray in communication with said at least one of the orifices and means for connecting the chamber to the fluid source.

* * * * *